(12) United States Patent
Kaufman

(10) Patent No.: US 9,925,149 B2
(45) Date of Patent: Mar. 27, 2018

(54) NANOPARTICLE COMPOSITIONS AND METHODS AS CARRIERS OF NUTRACEUTICAL FACTORS ACROSS CELL MEMBRANES AND BIOLOGICAL BARRIERS

(71) Applicant: NanoSphere Health Sciences, LLC, Greenwood Village, CO (US)

(72) Inventor: Richard Clark Kaufman, Santa Monica, CA (US)

(73) Assignee: NANOSPHERE HEALTH SCIENCES, LLC, Greenwood Village, CO (US)

( * ) Notice: Subject to any disclaimer, the term of this patent is extended or adjusted under 35 U.S.C. 154(b) by 0 days.

(21) Appl. No.: 15/029,566

(22) PCT Filed: Oct. 14, 2014

(86) PCT No.: PCT/US2014/060551
§ 371 (c)(1),
(2) Date: Apr. 14, 2016

(87) PCT Pub. No.: WO2015/057751
PCT Pub. Date: Apr. 23, 2015

(65) Prior Publication Data
US 2016/0263047 A1    Sep. 15, 2016

Related U.S. Application Data

(60) Provisional application No. 61/890,773, filed on Oct. 14, 2013.

(51) Int. Cl.
| | | |
|---|---|---|
| A61K 9/127 | (2006.01) |
| A61K 9/51 | (2006.01) |
| A61K 9/00 | (2006.01) |
| A61K 36/00 | (2006.01) |
| A61K 31/047 | (2006.01) |
| A61K 31/05 | (2006.01) |
| A61K 31/07 | (2006.01) |
| A61K 31/122 | (2006.01) |
| A61K 31/185 | (2006.01) |
| A61K 31/198 | (2006.01) |
| A61K 31/202 | (2006.01) |
| A61K 31/23 | (2006.01) |
| A61K 31/352 | (2006.01) |
| A61K 31/353 | (2006.01) |
| A61K 31/355 | (2006.01) |
| A61K 31/375 | (2006.01) |
| A61K 31/385 | (2006.01) |
| A61K 31/4172 | (2006.01) |
| A61K 31/4415 | (2006.01) |
| A61K 31/675 | (2006.01) |
| A61K 31/685 | (2006.01) |
| A61K 31/7034 | (2006.01) |
| A61K 31/728 | (2006.01) |
| A61K 33/06 | (2006.01) |
| A61K 33/24 | (2006.01) |
| A61K 33/30 | (2006.01) |
| A61K 36/16 | (2006.01) |
| A61K 36/185 | (2006.01) |
| A61K 36/28 | (2006.01) |

(Continued)

(52) U.S. Cl.
CPC ............ *A61K 9/5192* (2013.01); *A61K 9/006* (2013.01); *A61K 9/0014* (2013.01); *A61K 9/0048* (2013.01); *A61K 9/0053* (2013.01); *A61K 9/127* (2013.01); *A61K 9/1277* (2013.01); *A61K 9/5123* (2013.01); *A61K 31/047* (2013.01); *A61K 31/05* (2013.01); *A61K 31/07* (2013.01); *A61K 31/122* (2013.01); *A61K 31/185* (2013.01); *A61K 31/198* (2013.01); *A61K 31/202* (2013.01); *A61K 31/23* (2013.01); *A61K 31/352* (2013.01); *A61K 31/353* (2013.01); *A61K 31/355* (2013.01); *A61K 31/375* (2013.01); *A61K 31/385* (2013.01); *A61K 31/4172* (2013.01); *A61K 31/4415* (2013.01); *A61K 31/675* (2013.01); *A61K 31/685* (2013.01); *A61K 31/7034* (2013.01); *A61K 31/728* (2013.01); *A61K 33/06* (2013.01); *A61K 33/24* (2013.01); *A61K 33/30* (2013.01); *A61K 36/00* (2013.01); *A61K 36/16* (2013.01); *A61K 36/185* (2013.01); *A61K 36/28* (2013.01); *A61K 36/286* (2013.01); *A61K 36/82* (2013.01); *A61K 38/063* (2013.01)

(58) Field of Classification Search
CPC .......................... A61K 9/1277; A61K 9/5192
See application file for complete search history.

(56) References Cited

U.S. PATENT DOCUMENTS 5,662,932 A    9/1997   Amselem et al.
5,716,637 A    2/1998   Anselem et al.
(Continued)

FOREIGN PATENT DOCUMENTS

WO    WO 2001/049268        7/2001
WO       2012066334 A1 *    5/2012
(Continued)

OTHER PUBLICATIONS

Kaufman, "Nanosphere delivery systems, Methods for Overcoming Bioavailability limitations, Nanosphere Delivery Systems", Aug. 2015.*

(Continued)

*Primary Examiner* — Carlos A Azpuru
(74) *Attorney, Agent, or Firm* — Swanson & Bratschun, L.L.C.

(57) ABSTRACT

Novel process and products thereby emplace nutraceutical factors within nanodelivery vehicles for various indications in mammals, including humans.

5 Claims, No Drawings

(51) Int. Cl.
*A61K 36/286* (2006.01)
*A61K 36/82* (2006.01)
*A61K 38/06* (2006.01)

(56) References Cited

U.S. PATENT DOCUMENTS

| | | |
|---|---|---|
| 2003/0096000 A1 | 5/2003 | Solis et al. |
| 2005/0266067 A1 | 12/2005 | Sengupta et al. |
| 2008/0113031 A1 | 5/2008 | Moodley et al. |
| 2009/0074824 A1 | 3/2009 | Vila Pena et al. |
| 2011/0071118 A1 | 3/2011 | Lichtenberger |
| 2012/0093931 A9 | 4/2012 | McGinnis et al. |
| 2012/0321670 A1 | 12/2012 | Doshi et al. |
| 2013/0095032 A1 | 4/2013 | Margalit et al. |
| 2014/0348926 A1 | 11/2014 | Hoffman et al. |
| 2017/0000744 A1 | 1/2017 | Kaufman |

FOREIGN PATENT DOCUMENTS

| | | |
|---|---|---|
| WO | WO 2012/066334 A1 | 5/2012 |
| WO | WO 2012/003003 A2 | 10/2012 |
| WO | WO 2005/063665 | 7/2013 |
| WO | WO 2013/105101 A1 | 7/2013 |
| WO | WO 2015/057751 A1 | 4/2015 |
| WO | WO 2016/100228 | 6/2016 |
| WO | WO 2016/144376 | 9/2016 |

OTHER PUBLICATIONS

International Search Report for PCT/US14/60551, dated Jan. 13, 2015, 23 pages.
Kaufman, Nanosphere delivery systems. Methods for overcoming bioavailability limitations: Nanosphere Delivery Systems, Aug. 2013, pp. 1-8.
U.S. Appl. No. 15/536,134, filed Jun. 15, 2017, Kaufman.

* cited by examiner

NANOPARTICLE COMPOSITIONS AND METHODS AS CARRIERS OF NUTRACEUTICAL FACTORS ACROSS CELL MEMBRANES AND BIOLOGICAL BARRIERS

CROSS-REFERENCE TO RELATED APPLICATIONS

This application is a 35 U.S.C. § 371 national phase application of PCT/US2014/060551 (WO 2015/057751) filed on Oct. 14, 2014, entitled "Nanoparticle Compositions and Methods as Carriers of Nutraceutical Factors Across Cell Membranes and Biological Barriers", which application claims the priority benefit of U.S. Provisional Application No. 61/890,773, filed Oct. 14, 2013, and entitled "Nanoparticle Compositions and Methods as Carriers of Nutraceutical Factors Across Cell Membranes and Biological Barriers", which is incorporated herein by reference in its entirety.

TECHNICAL FIELD

The present disclosure teaches new methods and uses for nutraceutical delivery utilizing nanoparticle delivery compositions. The present disclosure relates to nanoparticles compositions and methods as efficient carriers of nutraceutical factors across cell membranes and biological barriers.

BACKGROUND

Delivery of nutraceuticals to the human body pose difficulty given bioavailability. Nutraceutical delivery is limited due to biokinetic and biodynamic reactions in the human body. Many nutraceuticals that contain antioxidant ingredients may be unstable, poorly water soluble, and poorly distributed in vivo. Delivery of nutraceuticals is important with regard to the overall efficacy of the nutraceutical. This disclosure teaches a novel nutraceutical delivery system.

SUMMARY OF THE EMBODIMENTS

The disclosure teaches a process for producing lipid structural nanoparticle carrier systems comprising a production method incorporating nanoparticle production schemes. This lipid structural nanoparticle carrier system is used for the delivery of nutraceuticals into mammals.

The disclosure teaches a nanoparticle technology for universal nutraceutical compositions. The process allows for assembling combination formulas of nutraceuticals with vastly different physical and molecular properties.

The production methods are selected from the group consisting of high shear homogenization and ultrasonication, high pressure homogenization, microemulsions, solvent emulsification/evaporation, water-in-oil double emulsion, product milling and the like. High pressure homogenization further comprises hot homogenization and cold homogenization.

The disclosure teaches a nanoparticle technology wherein the production method comprises a combination of milling, homogenation and ultrasonic processing in sequence, using cold techniques in each step.

At least one nutraceutical is incorporated into the process, effective for administration to mammals. Further, this disclosure teaches the products, by the process disclosed above, further comprising at least an additional supplement, vitamin and related compound safe to administer to mammals. In one embodiment, the disclosure teaches a combination of nutraceuticals. The combination of nutraceuticals comprises formulas of nutraceuticals with distinct and/or different physical and molecular properties.

The disclosure teaches a nanoparticle method of assembly wherein the assembly comprises three assembly techniques in a sequential unified process without the use of heat, without using solvents and/or polymers that encapsulate multiple species of nutraceuticals with essential phospholipids, fatty acids and solvents that are FDA approved.

In one embodiment, the disclosure teaches a nanosphere compositional structure of essential phospholipids and fatty acids and solvents that are FDA approved.

In one embodiment, the disclosure teaches a method of assembly for nano sphere compositional structures wherein the method of assembly efficiently encapsulates multiple species of nutracueticals that include water soluble vitamins, fat soluble vitamins, macro minerals, trace elements, phytochemicals, amino acids, fatty acids, peptides, botanical extracts and other nutraceuticals into a stable nanoparticle structure with a particle size distribution from 50 to 150 nm. This method of assembly allows for commercial production. The encapsulated material may have dissimilar molecular structures and physical properties. The differences in physical properties can include hydrophobic and hydrophillic moieties.

The disclosure teaches the products produced by the disclosure elucidated above. The disclosure teaches nanosphere compositional structure of essential phospholipids and fatty acids and solvents and method of assembly encapsulating multiple species of nutraceuticals containing hydrophilic and hydrophobic nutraceutical raw ingredients; and nutraceutical raw ingredients that are supplied as both solid and powders and liquids; into a stable nanoparticle structure that can be scaled for commercial sale.

The disclosure teaches a nanoparticle method of assembly wherein the assembly comprises three nanoparticle assembly techniques in a sequential unified process encapsulating multiple species of nutraceuticals. The nanoparticles are stable nanoparticle compositional structures with a particle size distribution from about 50 to 150 nm. The assembly can be scaled for commercial production and scalable to commercially available size production.

The disclosure teaches a nanoparticle composition structure and method of assembly encapsulating multiple species of nutraceuticals producing a stable nanoparticle composition with a high concentration of active nutraceutical factors to structure material; this ratio is in the range of about 1:3 to about 1:1. The disclosure teaches a nanosphere gel, with a viscosity and specific gravity for application for intraoral administration via the sublingual and/or buccal oral mucosa via a dropper or pump bottle that can be commercially sold/scaled. The disclosure teaches concentrated low volume delivery of the nanoparticle composition.

The disclosure teaches a universal platform for encapsulation of a broad range of unique and/or multiple species of nutraceuticals, and nutraceuticals having different molecular structures and physical properties without requiring changing the basic chemistry of the nanoparticle structure and method of assembly, that is commercially sold.

The disclosure further teaches the products for administration via the sublingual mucosa and buccal mucosa of a mammal. The disclosure further teaches a product, by the process disclosed above, for administration across ocular barriers and to ocular tissues. The disclosure further teaches a product, by the process disclosed above, for administration across dermal and epidermal barriers. The disclosure further teaches a product, by the process disclosed above, for administration across the blood brain barriers (BBB). The disclosure further teaches a product, by the process disclosed above, for administration across the gastrointestinal (GI) tract mucosal barrier. The disclosure further teaches a product, by the process disclosed above, for administration from the mouth directly to the jugular vein.

The disclosure further teaches a method for producing a nutraceutical for delivery via the sublingual mucosa and buccal mucosa of a mammal. The disclosure further teaches a method for producing a nutraceutical for administration across ocular barriers and to ocular tissues of a mammal. The disclosure further teaches a method for producing a nutraceutical for administration across dermal and epidermal barriers. The disclosure further teaches a method for producing a nutraceutical for administration across the BBB. The disclosure further teaches a method for producing a nutraceutical for administration across the GI tract mucosal barrier. The disclosure further teaches a method for producing a nutraceutical for administration from the mouth directly to the jugular vein.

The disclosure further teaches a method for the preparation of delivery system for nutraceuticals comprising encapsulating nutraceuticals in lipid structured nanoparticles for the transport of nutracueticals and drugs into a mammal or human.

The disclosure further teaches a method of administering lipid structured nanoparticles containing nutraceuticals to the oral mucosa for transport into the systemic circulation. Methods of administering of lipid structured nanoparticles in this disclosure are by liquid pump dispenser, liquid dropper, and spray pump dispenser, and any device that can administer lipid-structured nanoparticles to the sublingual or buccal oral mucosa.

The disclosure teaches formulating lipid structured nanoparticles containing nutraceuticals into solid dose forms including dissolvable tablets, granules lozenges, pellets, and other forms for intraoral delivery by sublingual and buccal administration. Suitable formulation methods include spray drying of lyophilization of lipid structured nanoparticle dispersions with suitable excipients followed by incorporation of a dry powder into a tablet or pellet. Another method is granulating lipid structured nanoparticles liquid dispersions with excipients and binders into powders for compression into tablets or pellets for sublingual and buccal delivery. Lipid structured nanoparticles may be incorporated into lozenges, lollipops, gum, gels and films for intra-oral delivery.

The disclosure further teaches the incorporation of lipid structured nanoparticles with pharmaceutical actives for intraoral sublingual and buccal delivery.

The disclosure further teaches a nanosphere comprising at least one of the following: multivitamin formulation, cholesterol control formulation, anti-arthritis and joint mobility formulation, sleep disorder formulation, anti-anxiety formulation, anti-depressive formulation, cognitive stimulant formulation, anti-ulcer formulation, acid reflux formulation, and/or weight loss/appetite control formulation. The additives or drugs included in these formulations may include, but are not limited to the following: Natural & Safe Alternative to Lipitor®, statins and lipid regulators for dyslipidemia and circulatory problems, Natural & Safe Alternative to Celebrex®, Lyrica®, NSAIDs and other arthritis drugs, Natural & Safe Alternative to Ambien®, Lunesta® & Sleep Meds for deep restorative sleep, Natural & Safe Alternative to Xanax®, Librium®, Valium®, Ativan® & benzodiazepines for anxiousness, stress, and restoring calm, Natural & Safe Alternative to Celexa®, Prozac®, Paxil®, Xolof®, Cymbalta®, Effexor®, Wellbutirn®, Elavil®, SNRIs and SSRIs for elevating depressive moods and mood disorders, Natural & Safe alternative to Aderall®, Ritalin® and stimulant medications for attention deficiency, mood disorders, behavioral problems, better cognition, focus, energy and higher performance, Natural & Safe alternative to Nexium®, Prilosec® and other ulcer meds, Natural & Safe Alternative to Xenical®, Sibutramine®, Rimonabant® and anti-obesity medications for losing weight.

DETAILED DESCRIPTION OF THE DISCLOSURE

Unless otherwise indicated, all numbers expressing quantities of ingredients, dimensions reaction conditions and so forth used in the specification and claims are to be understood as being modified in all instances by the term "about".

Percentages (%) refer to weight percent of the formulation.

In this application and the claims, the use of the singular includes the plural unless specifically stated otherwise. In addition, use of "or" means "and/or" unless stated otherwise. Moreover, the use of the term "including", as well as other forms, such as "includes" and "included", is not limiting. Also, terms such as "element" or "component" encompass both elements and components comprising one unit and elements and components that comprise more than one unit unless specifically stated otherwise.

The term "nanoparticle" in the present disclosure refers to different types of compositions of nano-scale particles as carriers that encapsulate or contain one or more nutraceutical supplements, by using a molecular assembly technique to carry the nutraceutical supplements across cell membranes and biological barriers to deliver the nutraceutical factors to target cell sites of the human body where they are released. Lipid nanoparticles are less than 150 nm in diameter.

Different types of "nanoparticle carrier compositions" that may be used as molecular carriers of nutraceutical factors in this disclosure include, but are not limited to, lipid structured nanoparticles made from essential phospholipids, fatty acids and solvents include, polymer nanoparticles and biodegradable polymers. Any "nanoparticle carrier" that is suitable for use in this disclosure may protect a nutraceutical factor from degradation, enhance factor absorption by facilitating diffusion through epithelium, modify the pharmacokinetic, and factor tissue distribution profile and/or improve intracellular penetration and distribution, and be GRAS listed and toxicity free.

Nanospheres refer to lipid nanoparticles that are mostly less than 100 nm diameter, and typically in the range of 50 nm to 150 nm. Nanopheres have high stability and minimal leakage of contents into the GI tract and blood. Nanospheres possess high long term stability. Nanospheres allow for high encapsulation of ingredients, and strong protection of ingredients. Nanospheres have a high degree of compatibility, versatility and usability for nutraceutical ingredients.

One embodiment of a "nanoparticle carrier" that is disclosed and used throughout this disclosure is known as lipid structured nanoparticles (solid lipid nanoparticles and lipid emulsion nanoparticles). These nanoparticle compositions are prepared from blending various suitable types of phospholipids and simpler lipids by using a molecular assembly technique known to those skilled in the art.

The term "nutraceutical factor" in this disclosure refers to any composition of one or more nutritional supplements, vitamins, vitamin derivatives and vitamin-like factors, minerals and derivatives, isolated nutrients, food factors (isolated or manmade), antioxidants (natural, synthetic, or semisynthetic), biological materials (structural compounds and derivatives, physiological chemicals, or metabolic factors), isoprenoids (carotenoids, tocopherols, tocotrienols, saponins, or terpanes), phenolic compounds (tannins, lignins, anthrocyanins, isoflavones, flavones, or flavonols), protein and amino acid factors (essential and non-essential protein, and protein derivatives like collagen, amino acids, peptides, indoles, or ally-s compounds), carbohydrates and derivatives (oligosaccahrides, glucans, mucopolysaccharides, glyconutrients, glucoproteins, chitin, chitosan, fructans, oligosaccharides, polysaccharides, chondroitan, or glucosamine), fatty acids, structured fats and lipids (essential fatty acids, essential oils, sphingolipids, lecithin, omega 3, 6, and 9, or PUFAs), phytonutrients and derivatives (phytochemicals, botanical compositions, algae, plankton, or chlorella), microbial nutraceuticals (prebiotics, probiotics, algae, fungi, or cyanobacteria), and other nutraceutical factors that are not listed.

The terms "cell membranes" and "biological barriers" in this disclosure refer to 1) the mucosal membrane barriers of the oral cavity; 2) the mucosal membrane barrier of the GI tract; 3) the dermal and epidermal cell membrane barriers; 4) the BBB; 5) the blood-ocular barrier consisting of the blood-aqueous barrier and the blood-retinal barrier; 6) ocular barriers of the conjunctiva and corneal epithelium; and 7) the cell membrane barriers of the nervous system, respiratory system, circulatory system, GI system, muscular system, urinary system, genital system, internal organs, and tissues.

The term mammal is intended to include, but not limited to, humans in this disclosure.

Nanoparticle Compositions

The preferred "nanoparticle carriers" for use in this disclosure are the lipid structured nanoparticles, solid lipid nanoparticles, and lipid emulsion nanoparticles. They are known to provide controlled release, efficient targeting, and stability to their cargo or payload.

"Solid lipid nanoparticles" essentially have a solid form. These dynamic structures are synthesized from natural lipid surfactants and contain an encapsulated inner core phase. They provide controlled release, efficient targeting, and stability to its cargo or payload.

"Lipid emulsion nanoparticles" are dynamic structured, dispersed particle droplets created from natural lipids that possess an outer phospholipid layer and an encapsulated inner lipid core.

Lipid structured nanoparticle assemblies may be dispersed in a solvent and carrier fluid during formulation. Suitable solvents and carrier fluids include water, sterile saline, glycerine, sorbitol, alcohol, lipids, fatty acids, polyglycols and silicone oils.

Lipid structured nanoparticles are constructed from phospholipids and simpler lipids. Phospholipid is the same material that comprises the major components of biological membranes and lipoproteins. As biological membranes, they exist as either sphingolipids or phosphodiglycerides. The most abundant phospholipid is phosphatidylcholine, also known as lecithin, and is the preferred phospholipid of these lipid structured nanoparticles in this disclosure.

The phospholipids in the process of synthesizing the lipid structured nanoparticle compositions in this disclosure may include phosphatidycholine, phosphatidylethanolamine, phosphatidylglycerol, phosphatidylserine, phosphatidylinositol, cardiolipin, and the derivatives of these phospholipids. Preferred phospholipids in lipid nanoparticles of this disclosure should be GRAS listed and non-toxic.

The simpler lipids in the process of synthesizing the lipid structured nanoparticle compositions in this disclosure may include fatty acids, triacylglycerols, acylglycerols, waxes, cholesterol, sphingolipids, and the derivatives of these lipids. Preferred simpler lipids in lipid nanoparticles of this disclosure should be GRAS listed and non-toxic.

The assembly of the lipid structured nanoparticle compositions in this disclosure may include materials and suitable emulsifiers such as polysorbates, monoglycerides, diglycerides, triglycerides, ethylene oxide/propylene oxide copolymers, sorbitan ethylene oxide/propylene oxide copolymers, alkylaryl, polyether alcohol polymers, bile salts, alcohols, and other surfactants that are known to the art. Preferred materials and emulsifiers in nanoparticles of this disclosure should be GRAS listed and non-toxic.

The assembly of the lipid structured nanoparticle compositions in this disclosure may include preservatives selected according to the route of delivery, barrier function, properties of nanoparticle materials, and properties of the encapsulated nutraceutical supplements. Plus, preservatives should be selected that do not induce changes in barrier functions, do not induce toxic and allergic effects, do not induce adverse effects to the nanoparticles, and do not induce adverse effects to the transported nutraceutical factors. Some of the preservatives for consideration in use include tocopherols, ascorbyl palmitate, sorbates, parabens, optiphen, thimersal, benzoic acid, bebzalkonium chloride, polyquaternium-1, ethyl lauroyl arginate, and rosemary oleoresin. Preferred preservatives of this disclosure should be GRAS listed and non-toxic.

Nanoparticle size is extremely important to the biological properties and functioning of the nanoparticle carriers of this disclosure. Nanoparticles with diameters ranging from 20 nm to 200 nm demonstrate the most prolonged circulation times. Nanoparticles are in the range from 20 nm to 100 nm. Nanoparticles are in the range from 20 to 60 nm Nanoparticles are in the range from 20 nm to 50 nm. Smaller nanoparticle sizes and a lipid structured nanoparticle composition can facilitate easier passage across cell membranes, enhancing cellular uptake and greater delivery to intracellular targets.

The assembly of lipid structured nanoparticle compositions in the present disclosure may include sweeteners for intraoral and peroral routes of delivery to enhance acceptability to the consumer. The sweeteners used may be natural sweeteners or artificial sweeteners. Natural sweeteners include xylitol, stevia, sucrose, fructose, fructooligosaccharides, glucose, glucose syrup, invert sugar, maltodextrins, Magnasweet, sorbitol, maltitol, lactitol, mannitol, and isomalt, Examples of artificial sweeteners include sucralose, aspartame, acesulfam K, neohesperidine, dihydrochalcone, thaumatin, saccharin and saccharin salts. Preferred sweeteners for this disclosure should be natural sweeteners such as xylitol, erythritol, stevia and Magnasweet. Typically the sweetener content will be (105 to 2.5% w/w.

The assembly of lipid structured nanoparticle compositions in the present disclosure may include flavors for intraoral and peroral routes of delivery to enhance acceptability to the consumer. The flavors used may be natural sweeteners or artificial sweeteners. Examples of flavoring agents useful in the compositions of the invention include fruit (e.g. pineapple or citrus) concentrates and concentrated aqueous or non-aqueous flavors such as flavor oils. Typically the sweetener content will be 0.1 to 2% w/w.

A smaller nanoparticle size (less than 60 nm), and a natural lipid and phospholipid nanoparticle composition (that mimics a plasma lipoprotein), can avoid extensive presystemic metabolism, avoid uptake by the reticuloendothelial system of the liver and spleen as a foreign substance, and prevent premature clearance from the body, is the preferred nanoparticle composition in this disclosure.

The process of synthesizing lipid nanoparticles in the present disclosure may include homogenization techniques such as hot high pressure homogenization technique, cold high pressure homogenization technique, melt emulsification ultrasound (ultrasonication) homogenization technique, high shear homogenization and/or ultrasound technique, microemulsion technique, emulsification-solvent evaporation technique, solvent displacement or injection technique, emulsification-solvent diffusion technique, phase inversion technique, film ultrasonication dispersion technique, and multiple emulsion technique. The disclosure teaches a method for manufacture of lipid nanoparticles a combination of three techniques, sequentially performed for dispersion comprising milling (physical grinding), homogenation (high speed stirring emulsification) and ultrasonic processing (high wattage flow through ultrasound sonification). These techniques can be performed in this sequential order or may be performed sequentially in alternate orders.

In one embodiment, the disclosure teaches the use of polymer nanoparticles as molecular carriers of nutraceuticals across cell membranes and biological barriers. The types of polymer nanoparticles are nanospheres and nanocapsules. Nanospheres have a monolithic-type structure (matrix) in which nutraceuticals are dispersed or adsorbed onto their surfaces or encapsulated within the particles. Nanocapsules are the vesicular system in which the nutraceutical drug is confined to a cavity consisting of an inner liquid core surrounded by a polymeric membrane. The ideal polymeric nanoparticle carriers for nutraceuticals are inexpensive, biocompatible, biodegradable, non-immunogenic, non-toxic, water-soluble, and constructed from GRAS materials.

In one embodiment, the types of polymers used for preparation of nanoparticles as carriers of nutraceuticals are natural hydrophilic polymers and synthetic hydrophobic polymers. Examples of natural hydrophilic polymers as carriers of nutraceuticals include proteins (gelatin, albumin, lecithin, legumin, and vicillin) and polysaccharides (alginate, dextran, chitosan, agarose, and pullulan). Examples of synthetic hydrophobic polymers as carriers of nutraceuticals include PLGA (poly-d,l-lactide-co-glycolide), PLA (Polylactic acid), PCL (poly-caprolactone), PAC (poly-alkyl-cyanoacrylates), poly-isobutyl cyanoacrylates, poly-butylcyanoacrylates and poly methyl(methcyanoacrylates). In one embodiment, polymers are not used in the preparation of nanoparticles as carriers of nutraceuticals.

The assembly methods of polymer nanoparticles may include solvent evaporation/solvent extraction technique interfacial deposition method, emulsion diffusion, nanoprecipitation, solvent displacement technique, double emulsion solvent evaporation method, spray drying, solvent evaporation method, emulsification solvent evaporative method, modified spontaneous emulsion solvent diffusion method, desolvation method, micelles, ionic gelation method, anionic polymerization, and salting out.

Transport Across Oral Mucosa Barriers

The disclosure provides a method of enhancing uptake into the blood stream of nutraceutical factors by administering the nanoparticle carrier composition to the sublingual mucosa and buccal mucosa of the oral cavity.

The nanoparticle carrier compositions of the disclosure enhance the absorption of nutraceutical supplements, nutraceuticals, nutrients, and phytonutrients through the sublingual mucosa, buccal mucosa and intestinal mucosa membranes into the bloodstream.

The disclosure teaches the increased dose-fraction of intraoral delivered nutraceutical factors across the oral mucosa into the systemic circulation in a nanoparticle carrier composition when compared to oral delivery of free factors through the GI into the systemic circulation.

Transport Across Ocular Barriers

The disclosure teaches a method for delivering nutraceutical factors for ocular functions across ocular barriers and to ocular tissues by employing a periocular nanoparticle carrier composition.

The disclosure also discloses methods for increasing transport across the conjunctival epithelial cell and corneal epithelium barriers of nutraceutical supplements by periocular administering the nanoparticle carrier compositions containing these factors.

The disclosure teaches methods and nanoparticle carrier compositions for periocular delivery of nutraceutical factors to the corneal epithelium and the conjunctiva that covers the sclera and lines the inside of the eyelids.

The disclosure also teaches methods and nanoparticle carrier compositions for periocular delivery of nutraceutical factors that play a role in visual functions and maintaining ocular structures.

The disclosure teaches the increased dose-fraction of periocular delivered nutraceutical factors past the blood-ocular barrier system to the cornea epithelium, to the conjunctiva and into ocular tissue in a nanoparticle composition when compared to oral delivery of free factors through the GI tract into the systemic circulation.

The disclosure also teaches a periocular nanoparticle carrier composition containing nutraceutical factors for enhancing transport across blood-ocular barriers and administered as part of an ophthalmic solution. A Periocular nanoparticle carrier system composition may also be formulated for intraoral administration across the oral mucosa.

Transport Across Dermal and Epidermal Barriers

The disclosure teaches methods for enhancing the transport of nutraceutical factors across epidermal cell barriers, across dermal cell barriers and into dermal cell structures by a transdermal nanoparticle carrier composition and administering in a topically applied liquid, cream, gel or ointment formulation.

The disclosure teaches the increased dose-fraction of transdermal delivered nutraceutical factors across the epidermal barrier into underlying dermal layers and dermal structures in a nanoparticle composition when compared to the transdermal delivery of free supplements.

Transport Across the Blood Brain Barrier

The disclosure teaches methods for enhancing the transport of nutraceutical factors across the BBB and the central nervous system in an intraoral or GI tract administered nanoparticle carrier composition that are described in other sections.

The disclosure teaches the increased dose-fraction of delivered nutraceutical factors across the BBB and into the central nervous system in a nanoparticle carrier composition when compared to the delivery of free factors across the BBB.

Transport Across the GI Tract Mucosal Barrier

The disclosure teaches methods for improving transport of encapsulated nutraceutical supplements across the mucosal membrane barriers of the GI tract into the bloodstream by oral administration of nanoparticle carrier composition. Another aspect of this disclosure relates to the increased dose-fraction of delivered nutraceutical factors across the mucosal membrane of the GI tract into the systemic circulation in a nanoparticle carrier composition when compared to the delivery of free factors across the mucosal membrane of the GI tract.

Transport Across Cell Membrane Barrier

The disclosure teaches methods for improving transport of encapsulated nutraceutical supplements across the cell membrane barriers of the nervous system, respiratory system, circulatory system, muscular system, urinary system, genital system, GI system, internal organs and tissues by administration of a nanoparticle carrier composition. Another aspect of this disclosure relates to the increased dose-fraction of delivered nutraceutical factors across the cell membrane barriers of the nervous system, respiratory system, circulatory system, muscular system, urinary system, genital system, GI system, internal organs and tissues, and into cell structures in a nanoparticle composition when compared to the delivery of free factors across the cell membrane barriers.

Intraoral Nanoparticles Delivery of Nutraceutical Factors Across the Oral Mucosa Barriers Within the mouth, the delivery of nutraceutical factors and drugs is classified into three categories: 1) Intraoral sublingual delivery, which is systemic delivery through the mucosal membranes lining the floor of the mouth; 2) Intraoral buccal delivery, which is administration through the mucosal membranes lining the cheeks (buccal mucosa); and 3) Perioral delivery, which is passage through the mouth into the gastrointestinal tract. Among these routes for delivering nutraceutical factors and nutraceuticals, the perioral route is most commonly used. However, the oral delivery of nutraceutical factors from the GI tract into the systemic circulation has numerous disadvantages. They include the acid-induced hydrolysis in the stomach, enzymatic degradation throughout the gastrointestinal tract, bacterial fermentation in the colon, and pre-systemic metabolism which significantly lowers bioavailability. Plus, the insolubility, hydrophobic nature, or molecular structure of certain compounds prevents their absorption from the GI tract. Data Array shows the primary factors that decrease the bioavailability and bio-effectiveness of the factors that you swallow.

The term "bioavailability" is the proportion that a substance is absorbed and detected in the systemic circulation after its administration. It does not refer to the bioeffectiveness of a substance.

Intraoral Delivery Through the Oral Mucosa

Intraoral delivery of nutraceutical supplements, nutraceuticals and pharmaceuticals through the mucosal linings of the oral cavity offers distinct advantages over peroral delivery through the GI tract. The oral mucosa is extremely rich in blood vessels and lymphatics that unlike the GI tract do not drain into the portal hepatic vein. Factors from the oral mucosa directly enter the systemic circulation from the jugular vein, thus avoiding passage through the liver where they may undergo undesirable metabolism (1'1 pass liver effect). Other tangible benefits include increased absorption, faster onset of actions, and greater bioavailability. Furthermore, intraoral delivery does not require swallowing and does not produce GI irritation.

Advantages of Intraoral Delivery

Increased bioavailability, higher plasma levels, rapid absorption and onset of actions, avoids pre-systemic elimination in the GI tract, avoids first-pass effect of the liver, avoids exposure to a hostile GI environment, and ability to swallow is not required.

From the Mouth Directly to the Jugular Vein

Delivering nutraceutical factors form the mouth to the jugular vein for systemic distribution is challenging. With sublingual or buccal administration, biological agents encounter the non-keratonized multilayered squamous epithelium of the oral mucosa. The ceils of the oral mucosa cells are bound together by small structures called desmosomes with a tight junction space of approximately 20 nm space between adjacent cells.

A continuous phospholipid membrane assembled into the upper third of epithelial cells and within the extracellular space forms a protective barrier of the oral mucosa. Luckily, the phospholipid membrane is permeable to lipophilic molecules and certain delivery system carriers. As a result, nutraceutical factors can readily diffuse through the phospholipid membrane of the oral mucosa into the systemic circulation.

In most cases, nutraceuticals and pharmaceuticals cross cell membranes of the oral mucosa by passive diffusion down a concentration gradient due to random molecular movements produced by thermal energy. The rate of transfer is directly proportional to the difference in concentration, and to the solubility of materials carried into the epithelial membranes. Active transport and pinocytosis through aqueous cellular pores plays a minimal role in transporting biological agents across the oral mucosa into the circulatory system.

The ability of molecules to permeate through the oral mucosa is related to molecular size, and ionization but to a lesser degree than the concentration gradient and lipid solubility. Small molecules, less than 250 daltons, appear to cross mucosa rapidly. As molecular size increases, the permeability decreases rapidly. Maximum absorption occurs when molecules are un-ionized or neutral in electrical charges. Highly polar molecules are insoluble in membrane lipids and unable to penetrate cellular membranes.

Permeation Differences Between the Sublingual and Buccal Mucosa

Anatomical and permeability differences between the sublingual and buccal mucosa necessitate different delivery system designs. Because of its high permeability and rich blood supply, the sublingual mucosa route gives fast absorption, a rapid onset of action, and overall high bioavailability. The sublingual mucosa is best suited for a delivery system of small particles providing a high concentration of compounds in a short delivery period time. Nano-sized solid lipid and droplet lipid nanospheres have an ideal composition and molecular structure for a sublingual delivery system.

The buccal mucosa is considerably less permeable than the sublingual area, and does not provide the rapid absorption and good bioavailability of sublingual administration. In several comparative studies, sublingual delivery was more effective than buccal delivery. The buccal mucosa is more suitable for a sustained release formulation and retentive delivery systems like bioadhesive polymers that adhere to the biological substrate at the site of absorption.

Transmucosal Nanoparticle Delivery of Nutraceutical Factors Across the Oral Mucosa The solution for delivering nutraceutical factors and nutraceuticals through the oral mucosa is encapsulating biological compounds into highly permeable lipid structured nanoparticles, such as a solid lipid nanoparticle sphere. A solid lipid nanoparticle sphere is formed from natural phospholipids and lipids, can be made with diameter of 25-50 nm, and is to administer to the mouth's sublingual oral mucosa via a controlled dropper device for rapid delivery across the oral mucosa and uptake into the circulatory system.

The lipid soluble structures of a solid lipid nanoparticle mimics plasma lipoproteins as a carrier system. Solid lipid nanoparticles, as well lipid emulsion nanoparticles, are highly permeable to the cell membrane and capable of encapsulating a high concentration of different nutraceutical factors for unimpeded rapid delivery through the oral mucosa. Some of the beneficial effects from a lipid nanoparticles delivery system are rapid absorption into the circulatory system, increased bioavailability, a fast onset of action, high plasma levels for a sustained period, and improved bioeffectiveness.

Lipid Nanoparticles have proven advantages as carriers that include:
 a) Increased bioavailability through transmucosal absorption and direct oral-cavity delivery;
 b) Sustained blood levels with greater bio-effectiveness and longer-lasting beneficial actions;
 c) Higher-potency responses, allowing reductions in amount and frequency of administration;
 d) Transport of blocked compounds across the BBB and into brain structures;
 e) Improved user convenience (less frequent use and easier compliance);
 f) Increased circulatory half-life (studies with pharmaceutical delivery loads have demonstrated up to 100-fold increases, resulting in dramatic rises in potency-up to 500-fold);
 g) Improved nutritional kinetics and dynamics, such as decreased enzyme degradation, prevention of hepatic metabolism to inactive byproducts, reduced renal clearance, and fewer adverse reactions;
 h) Site-specific actions that minimize loss of biological activity and expand therapeutic potential;
 i) Unique molecular "stealth technology," cloaking from the mononuclear phagocytic system and enzymatic destruction, thus prolonging and increasing the beneficial effects;
 j) Reduced adverse effects—decreased allergic reactions, side effects, and potential liver toxicity; and
 k) Improved cost-effectiveness on a per-unit amount.

Periocular Nanoparticle Delivery of Nutraceutical Factors for Ocular Structures and Functions Across Ocular Barriers The disclosure teaches a method for delivering nutraceutical factors for ocular functions that will be referred to as "ocular nutraceuticals" across ocular barriers and to ocular tissues by employing a periocular nanoparticle delivery system composition.

Many ocular nutraceuticals, when administered orally through the GI tract in their typical dosage forms, have low plasma bioavailability and limited delivery from the systemic circulation past blood ocular barriers to ocular tissues. Consequentially, this can inhibit their actions in maintaining ocular structures and essential visual functions.

The oral administration of ocular nutrients through the GI tract faces many obstacles that can prevent them from reaching ocular tissues. The systemic bioavailability of an ocular nutraceutical depends first on its solubility and absorption in the GI tract. Because many ocular nutrients are hydrophobic (averse to water), making them insoluble in aqueous solutions, they demonstrate slow or incomplete dissolution in the GI tract. Furthermore, an ocular nutraceutical may undergo pre-systemic metabolism upon oral administration that keeps plasma levels low despite a high intake.

Next, the insolubility, hydrophobic nature, size, shape, or molecular structure of an ocular nutraceutical can severely inhibit passage across blood-ocular barriers and delivery to ocular tissues. The blood-ocular barrier is a combination of microscopic structures within the eye which separates it from the rest of the body. The blood-ocular barrier system is formed by two main barriers: 1) the blood-aqueous barrier which regulates solute exchange between blood and intraocular fluid; and 2) the blood-retinal barrier which separates the blood from the neural retina. Both ocular barriers contain epithelial and endothelial components whose tight junction limits the transport of many molecules. They combine to maintain the eye as a privileged site and are essential for normal visual function.

This disclosure circumvents the delivery challenges of orally administered ocular nutrients to ocular tissue by administering lipid structured nanoparticles containing ocular factors and nutrients in the form of either a solid lipid nanoparticle or lipid emulsion nanoparticle carrier composition. The disclosure provides a new method with many advantages for delivering ocular factors and nutrients to ocular tissues by employing a properly formulated periocular lipid structured nanoparticle composition.

Nanoparticle Delivery of Nutraceutical Factors for Neural Structures and Functions Across the Blood-Brain Barrier The brain needs a barrier that separates it from the blood in order to permit the rigorous control of the brain microenvironment that is necessary for complex neural signaling. The BBB is an endothelial barrier present in the capillaries that course through the brain. It closely oversees what enters the brain from the rest of the body.

The BBB allows only required elements, such as nutrients and proteins used by the brain, to enter the brain's capillaries, turning a myriad of other blood borne molecules away. In its task of protecting the chemistry of the brain, the BBB barricades many beneficial compounds. According to an article in Nature Reviews: Drug Discovery by William Pardridge, the BBB prevents the brain uptake of >98% of all potential neurotherapeutics. These problems have led researchers to develop new delivery technologies to pass the BBB's well-guarded gates of the central nervous system.

The capillary endothelial cells that make up the BBB form very light, high resistance junctions that line the blood vessels that run through the brain. They act as a continuous lipid blockade, preventing the free diffusion through extracellular pathways that occurs regularly at most other organs. According to ultrastructural studies, endothelial cells in the brain differ fundamentally from those in most peripheral tissues in two ways. First, they have very few endocytotic vesicles, thereby limiting the amount of transcellular flux. Second, they are coupled by light junctions or zipper-like structures that seal the cleft and restrict paracellular flux.

For a molecule to diffuse through the BBB, it must have a sufficient amount of lipid solubility. In addition, the larger it is, the more difficult diffusion will be (no matter its solubility characteristics). However, highly lipophilic, small molecules cannot fulfill all the needs of a functioning brain. Small polar molecules, such as glucose and amino acids, and larger proteins, like insulin and transferrin, are also vital to the workings of the brain. These types of compounds must use more refined "gate keeping" processes to become part of the blood brain chemical traffic. Each of the required small molecules has its own transporter proteins expressed at the BBB that whisk it through the cell membranes in a process called carrier-mediated transport.

There are three different classes of endogenous transport systems within the BBB: 1) carrier-mediated transport systems; 2) receptor-mediated transcylosis (RMT) systems; and 3) active efflux transporters (AETs).

Normally, the tight junctions of the BBB permit the diffusion of only very small amounts of water-soluble compounds (paracellular aqueous pathway), while the large surface area of the lipid membranes of the endothelium offers an effective diffusive route for lipid-soluble agents (transcellular lipophilic pathway).

A practical route through which a substance may cross the endothelium is by the transcellular lipophilic pathway. There is a good correlation between BBB penetration in vivo and the lipid solubility of a compound or molecular structure. Molecules that are small enough and lipid-soluble enough can slip through the BBB in pharmacologically significant amounts.

A lipid structured nanoparticle composition represents a practical carrier system for delivering compounds to the brain via the transcellular lipophilic pathway. Lipid structured nanoparticle compositions can not only circumvent the BBB limiting characteristics of the carried molecule, but can also protect it from chemical/enzymatic degradation, and additionally provide the opportunity for sustained release characteristics. A wide range of drugs have been formulated into lipid structured nanoparticle compositions and have proven to pass the BBB in high dosage percentages.

Transdermal Nanoparticle Delivery of Nutraceutical Factors for Dermal Structures and Functions Across Skin Barriers Lipid structured nanoparticles are the new generation of nanoparticulate active substance vehicles and are attracting major attention as practical colloidal carriers for topical use. Small lipid nanoparticle vesicles in the range of nanometers have the advantages, but avoid the disadvantages of other colloidal carriers. Solid lipid nanoparticles were developed at the beginning of the 1990s as an alternative carrier system to emulsions, liposomes, and polymeric nanoparticles. During recent years, solid lipid nanoparticles have been used in topical cosmetic products.

Compared with polymeric nanoparticles, solid lipid nanoparticles and lipid emulsion nanoparticles have lower toxicity because of the absence of solvents in the production process, and are also relatively less expensive for the excipients. Solid lipid nanoparticles and lipid emulsion nanoparticles represent particulate carrier systems which can be produced with an established technique, allowing production on an industrial scale that also protects the incorporated compound drug against chemical degradation.

Stratum corneum is the main barrier in the percutaneous absorption of topically applied compounds. Small size and relatively narrow size distribution of solid lipid nanoparticle carriers permit site-specific delivery to the skin. Solid lipid nanoparticles have high affinity to the stratum corneum, and therefore an enhanced bioavailability of the encapsulated material to the skin is achieved. Solid lipid nanoparticles enhance the penetration and transport active substances, particularly lipophilic agents and thus, intensify the concentration of these agents in the skin.

The barrier layers of the stratum corneum mainly consist of ceramides, cholesterol and palmitic acid. They occur in the form of bilayers. The dermaceutical carrier system of skin care with the same factors, or at least a similar composition, also forms bilayers.

Ceramides are the most important intercellular lipids of the stratum corneum, regulating the barrier function of the skin and participating as second signal messenger in stress-induced apoptosis. The high lipophilicity of ceramides enable their incorporation into a lipid nanoparticle for transport across the stratum corneum to deeper skin layers for pharmacological effects.

Solid lipid nanoparticles as well as lipid emulsion nanoparticles carriers that are formed from phosphatidylcholine are superior dermal carriers. Interestingly, phosphatidylcholine shows properties which are similar to the properties of ceramides. It integrates in the skin barrier layers, and just like the ceramides, it is very resistant against exogenous substances. Nanoparticles, which contain phosphatidylcholine as a raw material, are very well integrated by the bilayers of the stratum corneum.

Because a lipid structured nanoparticle composition can be formed with non-toxic and non-irritant lipids like phosphatidylcholine of GRAS status, they are well suited for use on damaged or inflamed skin, and may reduce the irritancy of some agents because of their controlled release properties.

The small particle size diameter a solid lipid nanoparticle carrier (<60 nm) helps ensure close contact to the stratum corneum and compounds encapsulated in lipids improve selective delivery to skin layers. Solid lipid nanoparticles possess a solid matrix, which has the potential to modulate the active compounds release over a prolonged period with a reduced rate of systemic absorption. Another benefit of a solid lipid nanoparticles carrier for topical delivery of active compounds is that the time-to market is very short for these products.

Lipid structured nanoparticles compositions have been proven to disperse skin regeneration supporting substances relatively quick into the horny layer and carry them into the deeper skin layers. The most frequently topically applied skin regeneration supporting substances are vitamins and related substances, as well as their esters. These produce greater benefits when incorporated into a lipid nanoparticle delivery system.

The list includes a wide range of nutraceutical factors (See Data Array 3).

Some of the benefits of lipid structured nanoparticles as carriers of topically applied agents:

a) Improved stability of chemically unstable active ingredients;
b) Delivery into deeper skin layers and target structures;
c) Controlled release of active ingredients;
d) Increased bioavailability and bioactivity; and
e) Improved skin hydration and protection through film formation on the skin.

Lipid Structured Nanoparticle Compositions

The interdisciplinary field of nanobiotechnology, combining chemistry, biology, engineering, and medicine, is revolutionizing the development of delivery systems for a wide range of biological agents from drugs to nutraceutical factors. Natural, non-toxic biomaterials with nanosize organization are being used to create nanoparticle delivery systems. Nanoparticle delivery systems can be synthesized with controlled composition, shape, size morphology, and surface properties to increase efficacy by improving oral absorption solubility, cellular penetration, site-specific targeting, and suboptimal bioavailability.

Nanoparticle delivery systems have enhanced ability to cross cell membranes, reduce the risk of undesired pre-systemic metabolism, avoid uptake by the Reticuloendothelial system of the liver and spleen as foreign substances, and prevent premature clearance from the body. They can be formed to cross the BBB into specific neurological sites. Plus, they can target GI abnormalities in the epithelial lining of the gut wall. Smaller nanoparticles have greater surface area-to-volume ratios, which increase the particles' dissolution rate, enabling them to overcome solubility-limited bioavailability.

Data Array 6 describes some of the representative different types of nanoparticle carriers.

Solid Lipid Nanoparticle Carriers

Solid lipid nanoparticle carriers essentially have a bilayer solid form. These lipoprotein-like dynamic structures are synthesized from natural lipid surfactants and contain a solid outer phospholipid layer that encapsulates an inner simpler lipid core. They provide controlled release, efficient targeting, and stability to its cargo or payload.

Because of the phospholipids ability to balance between hydrophilic and lipophilic properties, phospholipids such as lecithin form the membrane layer of nanospheres that surround a lipid core. The lipophilic fatty acids of the phospholipids are arranged in the interior membrane of the nanosphere and the hydrophilic head groups of the phospholipid molecules are orientated towards the exterior. A lipophilic inner core consists of simpler lipids. The lipophilic interior of the outer membrane and inner core of the nanosphere makes it possible to incorporate high levels of the nutraceutical substance. Nutraceutical substance can be up to 40%. Nutraceutical substance can be up to 50%. Nutraceutical substance can be up to 60%. Nutraceutical substance can be up to 70%. Nutraceutical substance can be up to 80%. Nutraceutical substance can be up to 90%. Nutraceutical substance can be up to 95%.

When solid lipid nanoparticles are combined with biological agents, they are a highly effective, unique carrier particle for systemic distribution including extravascular transit and targeted cell uptake. Because of the small uniform size, they are rapidly absorbed intra-orally, dermally or through the GI tract. They avoid pre-systemic metabolism, avoid uptake by the Reticuloendothelial system, exhibit superior systemic distribution, readily enter body structures, and pass efficiently into cells to target sites to deliver their payload.

Solid lipid nanoparticle carriers can easily be formed that show a great similarity to endogenous plasma lipoproteins in composition, size, morphology, and surface properties as a carrier system. They are subject to the same cellular uptake process into numerous tissues and organs that occur by a transport mechanism known as receptor-mediated endocytosis. Because they have a very small particle size, they can even pass easily through a leaky capillary wall.

Some of the documented advantages of solid lipid nanoparticle carriers include:

a) Increased bioavailability through transmucosal absorption and direct oral-cavity delivery;
b) Sustained blood levels with greater bio-effectiveness and longer-lasting beneficial actions;
c) Higher-potency responses, allowing reductions in amount and in frequency of administration;
d) Increased efficacy of ingredients through site targeting;
e) Transport of blocked compounds across the blood-brain barrier and into brain structures;
f) Improved user convenience (less frequent use and easier compliance);
g) Increased circulatory half-life (studies with delivery loads have demonstrated up to 100-fold increases. resulting in dramatic rises in potency-up to 500-fold);
h) Circulation times in vivo extended from hours to days, improved nutritional kinetics and dynamics such as decreased enzyme degradation, prevention of hepatic metabolism to inactive byproducts, reduced renal clearance, and fewer adverse reactions;
i) Site-specific actions that minimize loss of biological activity and expand therapeutic potential;
j) Unique molecular "stealth technology," cloaking from the mononuclear phagocytic system and enzymatic destruction, thus prolonging and increasing the beneficial effects;
k) Reduced adverse effects: decreased allergic reactions, side effects, and potential liver toxicity;
l) Improved cost-effectiveness on a per-unit amount; and
m) Precision metering in small incremental amounts.

Lipid Emulsion Nanoparticle Carriers

Lipid emulsion nanoparticle carriers are dynamic structured, dispersed particle droplets created from natural lipids that possess an outer phospholipid layer and an encapsulated inner lipid core.

An emulsion is a liquid system in which one liquid is dispersed into a second, immiscible liquid (with or without emulsifiers), usually in droplets. A typical parenteral lipid emulsion consists of a water phase with droplets composed of a triglyceride core (diameter 250-450 nm) stabilized with a phospholipid monolayer (2-3 nm). The phospholipid monolayer stabilizes the emulsion by long-range, repulsive electrostatic forces and short-range, repulsive hydration forces.

Lipid emulsion nanoparticle carriers can be formed with a composition, droplet size and distribution that are much like those of chylomicrons (75-400 nm), the endogenous aggregates that distribute lipids in the bloodstream. Lipid emulsion nanoparticle carriers can be formed with a small mean droplet size of 75-140 nm that are similar to chylomicrons, although the droplet size distribution is wider for chylomicrons. In both systems, phospholipids are the emulsifier. Lipid emulsion nanoparticle carriers can also be formed with a smaller mean droplet size of <75 nm.

Some of the documented advantages of lipid emulsion nanoparticle carriers include:

a) Sustained blood levels with greater bio-effectiveness and longer-lasting beneficial actions;
b) Protection of agents from the hostile environment and degradation in the gut;
c) Increased efficacy of ingredients through site targeting that expands the therapeutic potential;
d) Improved nutritional kinetics and dynamics;
e) Much higher surface area and free energy than macroemulsions that make them an effective transport system;
f) Increased tissue penetration over micron-sized regular emulsions;
g) Increased effectiveness of the delivered agent that may result in a reduction in dose and frequency of administrations to achieve results;
h) Reduced adverse effects; and
i) Improved cost-effectiveness on a per-unit amount.

The disclosure further teaches a method of administering lipid structured nanoparticles containing nutraceuticals to the oral mucosa for transport into the systemic circulation. Methods of administering of lipid structured nanoparticles in this disclosure are by liquid pump dispenser, liquid dropper, and spray pump dispenser, and any device that can administer lipid-structured nanoparticles to the sublingual or buccal oral mucosa.

Precise dosages of lipid structured nanoparticles should be administered to the sublingual mucosa and buccal mucosa. The dose of a lipid-structured nanoparticle solution per each administration may range from 50 mcl to 1000 mcl of fluid. The preferred amount per dose of lipid-structured nanoparticle solution is between 130 mcl and 450 mcl. (1 ml=1000 mcl)

The disclosure further teaches the method of administering lipid structured nanoparticles to the oral mucosa for transport into the systemic circulation. The methods of administering of lipid-structured nanoparticles in this disclosure are by liquid pump, liquid dropper and spray pump apparatus and any device that can deliver lipid-structured nanoparticles to the sublingual or buccal oral mucosa. Precise dosages of lipid-structured nanoparticles are administered to the sublingual mucosa and buccal mucosa. The dosage of a lipid-structured nanoparticle solution per each administration may range from 59 mcl to 1000 mcl of fluid. The preferred embodiment per dose of lipid-structured nanoparticle solution is between 130 mcl and 450 mcl.

The disclosure teaches swallowing a nanosphere liquid or soft gel capsule filled with a liquid. The dose range is 1 ml to 10 ml.

The disclosure teaches formulating lipid structured nanoparticles containing nutraceuticals into solid dose forms including dissolvable tablets, granules, lozenges, pellets, and other forms for intraoral delivery by sublingual and buccal administration. Suitable formulation methods include spray drying of lyophilization of lipid-structured nanoparticle dispersions with suitable excipients followed by incorporation of the dry powder into the tablet, or pellets. Another method is granulating lipid-structured nanoparticles liquid dispersions with excipients and binders into powders for compression into tablets or pellets for sublingual and buccal delivery. Lipid-structured nanoparticles may be incorporated into lozenges, lollipops, gum, gels and films for intra-oral delivery.

EXAMPLES

The following examples are provided for illustrative purposes only and are not intended to limit the scope of the invention.

Example 1 Examples of Nutraceutical Factors for Delivery Across the Oral Mucosa and Into the Systemic Circulation in an Intraoral Nanoparticle Carrier Composition Data Array 1

Examples of nutraceutical factors for delivery across the oral mucosa and into the systemic circulation in an intraoral nanoparticle carrier composition include one or more of the following:

Essential Fatty Acids—Omega-3 EPA and DHA, omega-6 GLA, CLA

Phytonutrients—curcumin, silymarin, andrographis, boswellin, green tea extract, blue corn color, cats claw extract, sambaia extract, grape seed extract, hawthorn berry extract, boswellin, haritaki extract, centella asiatica extract, pine bark extract, pomegranate extract, ginkgo biloba extract, bilberry extract, rosemary extract, bitter melon extract, astragulus extract, cats claw extract, cranberry extract, mushroom extracts, citrus seed extract, ashwagandha extract, bitter melon fruit extract, black cohosh extract, cordyceps extract, vitex agnus castus extract dandelion root extract, epimedium extract, garcinia cambogia extract, ginger extract, gymnema sylvestre leaf extract, irvingia gabonensis extract, kola nut extract, licorice root extract, maca root extract pomegranate extract, rhodiola rosea extract, saw palmetto fruit extract, siberian ginseng root extract, green coffee bean extract, kola nut extract, licorice root extract, maca root extract, muira puama bark extract, schizandra berry extract. tribulus terrestris extract, uva ursi leaf extract, yerba mate extract, cinnamon extract, hawthorn extract, miura puama extract, cnidium extract, angelica sinensis extract, tumeric extract, ajuga turkestanica, algae extract, aralia mandshurica extract, artichoke extract, bitter melon extract, ajuga tukestanica, corioius vesicolor extract, cramp bark extract, eurcoma longifolia jack extract, horsetail extract, lentinula adode extract, cranberry extract, St. John's Wort extract, Japanese knotwood extract, maitake extract, ganoderma extract, momordica charantia extract, olive leaf extract, panax ginseng extract, pasiflora incarnata extract, pau d'arco extract, pygeum extract, prunus africanus extract, rhaponticum cathaomids extract, ruscus aculeatus extract, stinging nettles extract urtica dioca extract, valerian extract, withania somnifera extract Phytochemicals—vinpocetine, forskolin, ellagic acid, resveratrol, quercetin, berberine, curcumin, hordenine, dihydromyrecetin, caffeine, gugullipids, arabinogalactans, icariin, huperzine a, osthole, iccarin, chrysin, DIM, PQQ, daidzein, dossgenein, fucoxanthin, genistein, huperzine, policosanol, pterostilbene, raspberry ketone, maslinic acid, octopamine, velvet deer antler, ellagic acid, glalantamine, silymarin, red yeast rice, glycyrrhizic acid, hesperidin methyl chalcone, myrecetin, natokinase, red wine poyphenols, rutin, 20-hydroxy ecdysterone Hormones—DHEA, 7-Keo DHEA, pregnenolone, melatonin Antioxidants—glutathione, alpha-lipoic acid R-lipoic acid, SOD, catalase, flavonoids, carotenoids, catechins, epicatechins Fat Soluble Vitamins—vitamins A, D, E, K1, K2

Water soluble Vitamins—vitamins B1, B2, B3, B5 B6 and B12, folate, pyridoaxal-5 phosphate, pantethine Vitamin Derivatives—benfotiamine Minerals—calcium, magnesium, iodine, iodide, chromium, selenium, potassium, silver, rhodium, molybdenum, manganese, iron, copper zinc, boron, vanadium, silicon, lithium, silver, strontium Fatty Acids—docosahexanoic acid, marine lipids, omega-3 and omega-6 fatty acids, blackcurrant seed oil, borage oil, evening primrose oil, hemp seed oil, cetyl myristoleate, conjugated linoleic acid, flax seed oil, phosphatidyserine, krill oil, fumaric acid, undecylenic acid, shark liver oil Carotenoids—lutein, lycopene, luteolin, beta-carotene, zeaxanthin, staxanthin Tocopherols—alpha-tocopherol, mixed tocopherols, tocotrienols Phytosterols—β-Sitosterol, Stigmasterol Metabolic Factors—glucosamine, chondroitin sulfate, hyaluronic acid, CoQ10, lipoic acid, beta-phenylethylamine, beta-glucan, L-carnosine, ferulic acid, gamma oryzanol, L-theanine, phenibut, forskolin, 5-hydroxy tryptophan, inositol hexaphosphate, alpha-glycerolphosphoryl choline, piracetam, L-tyrosine, N-acetyl tyrosine, L-carnitine, adenosine triphosphate, fucoidan, TMG. DMG, vaadyl sulfate, uridine-5-monophosphate, calcium 2-AEP, collagen type II, serapeptase, thymic protein A, uridine, 5-HTP, GABA, hyaluronic acid, DMAE Chelators—EDTA, DMSA Basic Intraoral Nanoparticle Carrier Composition Formulation 1-60% Nutraceutical Factors (Factors in Data Array 1 such as Resveratrol)

20-75% Phospholipids (Lipoid Phospholipon 90 G, Lipoid Phospholipon 90 H, Lipoid S 75, Lipoid S 40, Lipoid S 80, Lipoid E 80, Lipoid Phosal 50 SA, Lipoid Phosal 53 MCT)

25-75% Lipids (Safflower Oil, Sunflower Oil, Medium Chain Triglycerides)0-20% Solvents and Carrier Fluid (Distilled Water, Ethanol Glycerin, TLipids)
0-5% Preservatives (Ascorbyl Palmitate, Rosemary oleoresin, Tocopherol, Potassium Sorbate)

Example 2 Examples of Nutraceutical Factors for Ocular Functions and for Delivery to Ocular Tissues in a Periocular Nanoparticle Carrier Composition Data Array 2
Examples of nutraceutical factors for ocular functions and for delivery to ocular tissues in a periocular nanoparticle carrier composition include one or more the following:
Antioxidants—N-acetyi-carnosine, L-giutathione. lipoic acid, N-acetylcysteine
Carotenoids—zeaxanthin, cryptoxanthin, lutein, astaxanthin
Flavonoids—hesperidin methyl chalcone
Amino acids—Mg taurate
Vitamins—vitamin E, vitamin A (retinol), vitamin C
Vitamin derivatives—pyridoxamine, benfotiamine, ascorbyl palmitate
Essential Minerals—zinc, selenium, magnesium
Mucopolysaccharides—sodium hyaluronate
Fatty Acids—DHA, EPA, GLA, black currant seed oil
Phytochemicals—resveratrol, quercetin, forskolin, silibinin
Phytonutrients—green tea extract, ginkgo biloba extract
Chelators—EDTA, DMSA Example 3 Basic Periocular Nanoparticle Carrier Composition in an Ophthalmic Solution Formulation 0.75-2% Antioxidant Factors (N-Acetyl Carnosine, Lipoic acid, L-Giutathione)
0.3-1.5% Carotenoid Factors (Zeaxanthin, Lutein)
0.3-1.5% Vitamin Factors (Vitamin E acetate, Retinyl acetate)
2-10% Phospholipids (Lipoid Phospholipon 90 G, Lipoid Phospholipon 90 H, Lipoid S 75, Lipoid E 80, etc.)
2-10% Lipids (Medium Chain Triglycerides, etc.)
0-20% Surfactants (Tween 80, etc.)
0-5% Preservatives (Polyquaternium-1, benzalkonium chloride)
0.1-0.6% Moisturizers (Hydroxypropyl Methylcellulose, Hydroxymethylcellulose, Carboxymethylcellulose, Glycerin)
0.8-1.2% Buffers (Boric Acid, Sodium Borate, etc)
0.8-1.6% Osmolarity Adjuster (Sodium Chloride, Potassium Chloride, Magnesium Chloride, Zinc Chloride, etc.)
The nutraceutical factors in this formulation are primary ocular antioxidants that inhibit oxidative stress and free radical damage that is known to play a role in corneal, macular and retinal pathology.
q.s. pH 7.4. Ph Adjuster (NaOH/HCl)
q.s. to 100% Carrier (Purified Water)

Example 4

Data Array 3
Examples of Nutraceutical dermal support and structure factors for delivery to skin cell structures in a transdermal nanoparticle carrier composition include one or more of the following:
Peptides—acetyl hexapeptide-8, pentapeptide-3, dipeptide diaminobutyroyl benzylamide diacetate, palmitoyl oligopeptide, palmitoyl tetrapeptide-, palmitoyl tetrapeptide-3, tripeptide-10 citrulline, tripeptide-1, hydrolyzed soy and wheat protein, pseudoalteromonas ferment extract, oligomers of soluble collagen, hydrolyzed fibronectin, acetyl tetrapeptide-5, hydrolyzed rice bran protein, rice peptides, soy peptides, oxide reductases, dipeptide valyitryptophane, lipopeptide pai-giy-gin-pro-arg, human oligopeptide-20, acetyl octapeptide-3, palmitoyl tripeptide-5
Vitamins and Vitamin Derivatives—vitamin A, vitamin C, vitamin C esters, L-ascorbyl 2-polyphosphate, vitamin E, tocotrienols, retinyl palmitate, retinyl acetate, vitamin E acetate, vitamin K, tetrahexyldecyl ascorbate
Mucopolysaccharides—sodium hyaluronate, hydrolyze glycosaminoglycans
Flavonoids—hesperidin methyl chalcone
Carotenoids—lycopene, lutein, beta-carotene
Fatty Acids—DHA, GLA, linolenic (essential fatty acid) triglyceride, oleic acid, unsaponifiable fraction of soybean oil, botrytis oil, evening primrose oil, EMU Oil, tea tree oil, glyceryl linoleate, glyceryl linolenate, glyceryl arachidonate
Lipids—ceramide 3, ceramide 611, ceramide 1, phytosphingosine, cholesterol, sodium lauroyl lactylate, C10-C18 triglycerides, PEG-4 EFA proline ester, squalane, squalene, cephalins
Phytonutrients and Phytochemicals—green tea extract, grape seed extract, daucus carota extract curcumin, 1-malic acid concentrated from cherries, bamboo extract, cocoa extract, cola (nut) extract, echinacea purpurea extract, ginkgo biloba leaf extract. rosemary extract, horse chestnut extract, silybum marianum fruit extract, turmerone
Amino acids—proline
Organic bound trace minerals—zinc, copper, magnesium and manganese aspartates, selenomethionine
Metabolites—ubiquinone, idebenone, DMAE. lipoic acid, CM-glucan, hydrolyzed fibronectin, hydrolyzed and soluble collagens, isodecyl salicylate, SLANOLs (methylsilanetriol derivatives), phenyl-butyl-nitrone, beta-glucan Example 5 Basic Transdermal Nanoparticle Carrier Composition in a Topical Gel Formulation 15-45% Peptides (Argireline®, Syn-ake®, Leuphasyl®, Trylagen®, Eyeseryl®, Matrixyl 3000®, Regu-Age®)***
10-30% Skin Factors (Apo-Carotenol, Ascorbyl Polyphophosphate, Hesperidin Methyl Chalcone)***
4-16% Skin Structure Materials (Collagenon®, Hyaluramine®, Dermanectin®)***
15-35% Phospholipids (Lipoid Phospholipon 90 G, Lipoid Phospholipon 90 H, Lipoid S 75, Lipoid E 80, Lipoid Phosal 50 SA, Lipoid Phosal 53 MCT)
10-45% Lipids (Medium Chain Triglycerides, Ceramides, Sk-Influx etc)***
0-10% Surfactants (Tween 80, Pluronic F68, Poloxamer 188, Ascorbyl-6 palmitate, etc)
0.5-1% Preservatives (Optiphen)
q.s. 100% Carrier (purified water)
The skin active ingredient in nutraceutical factors in examples such as this formulation is formulated into lipid nanoparticle carriers as a facial serum formulation. Their documented actions can decrease the appearance of expression wrinkles, crow's feet, skin dryness, fine lines, eye puffiness, eye-bags, hyper-pigmentations, and blemishes; while adding firmness, hydration stratum corneum barrier reconstitution to the skin, and increased protection of the skin against cutaneous skin aging, harmful free radical dermal damage, undesirable cross linked molecules, inflammation, and UV solar radiation aging damage.

Example 6

Data Array 4

Examples of nutraceutical factors for delivery past the BBB in a nanoparticle carrier composition include one or more the following:

Phytochemicals—vinpocetine, phenylethylamine, galatamine, huperzine A, reseveratrol, hordenine Phytonutrients—ginkgo biloba extract, bacopa minnieri extract, rhodiola rosea extract, St. John's Wort extract Vitamins—vitamins A, C, E, D, B6 and B12, folate Fatty Acids—docosahexanoic acid, phophatadylserine Metabolic Factors—CDP choline, idebenone, acetyl-L-carnitine, CoQ10, DMAE, theanine, 5-HTP, phenibut, alpha glycerophospocholine, L-tyrosine Chelators—EDTA

Example 7

Examples of Nutraceutical Factors for Delivery Past GI Tract Oral Mucosa Into the Systemic Circulation in a Nanoparticle Carrier Composition 1-60% Nutraceutical Factors (Factors in Data Array 1, Such as CDP Choline):

20-75% Phospholipids (Lipoid Phospholipon 90 G, Lipoid Phospholipon 90 H, Lipoid S 75, Lipoid S 40, Lipoid S 80, Lipoid E 80, Lipoid Phosal 50 SA, Lipoid Phosal 53 MCT)

25-75% Lipids (Safflower Oil, Sunflower Oil, Medium Chain Triglycerides)

10-50% Solvents and Carrier Fluids (Distilled Water, Ethanol, Glycerine, Lipids)

0-5% Preservatives (Ascorbyl Palmitate, Rosemary oleoresin, Tocopherol, Potassium Sorbate)

This formulation is designed for peroral administration to the sublingual mucosa and buccal mucosa of the oral cavity.

Data Array 5

Examples of nutraceutical factors for delivery past GI tract oral mucosa into the systemic circulation in a Nanoparticle carrier composition include one or more of the following:

Phytonutrients—curcumin, silymarin, andrographis, boswellin, green tea extract, blue corn color, cats claw extract, sambaia extract, grape seed extract, hawthorn berry extract, boswellin, haritaki extract, centella asiatica extract, pine bark extract, pomegranate extract, ginkgo biloba extract, bilbery extract, rosemary extract, bitter melon extract, astragulus extract, cats claw extract, cranberry extract, mushroom extracts, citrus seed extract, ashwagandha extract, bitter melon fruit extract, black cohosh extract, cordyceps extract, vitex agnus castus extract dandelion root extract, epimedium extract, garcinia cambogia extract, ginger extract, gymnema sylvestre leaf extract, irvingia gabonensis extract, kola nut extract, licorice root extract, maca root extract pomegranate extract, rhodiola rosea extract, saw palmetto fruit extract, siberian ginseng root extract, green coffee bean extract, kola nut extract, licorice root extract, maca root extract, muira puama bark extract, schizandra berry extract. tribulus terrestris extract, uva ursi leaf extract, yerba mate extract, cinnamon extract, hawthorn extract, miura puama extract, cnidium extract, angelica sinensis extract, tumeric extract, ajuga turkestana, algae extract, aralia mandshurica extract, artichoke extract, bitter melon extract, ajuga tukestanica, corioius vesicolor extract, cramp bark extract, eurcoma longifolia jack extract, horsetail extract, lentinula adode extract, cranberry extract, St. John's Wort Extract, Japanese Knotwood extract, maitake extract, ganoderma extract, momordica charantia extract, olive leaf extract, panax ginseng extract, pasiflora incarnata extract, Pau D'Arco extract, pygeum extract, prunus africanus extract, rhaponticum cathaomids extract, ruscus aculeatus extract, stinging nettles extract, urtica dioca extract, valerian extract, withania somnifera extract Phytochemicals—vinpocetine, forskolin, ellagic acid, resveratrol, quercetin, berberine, curcumin, hordenine, dihydromyrecetin, caffeine, gugullipids, arabinogalactans, icariin, huperzine A, osthole, iccarin, chrysin, DIM, PQQ, daidzein, dossgenein, fucoxanthin, genistein, huperzine, policosanol, pterostilbene, raspberry ketone, maslinic acid, octopamine, velvet deer antler, ellagic acid, glalantamine, silymarin, red yeast rice, glycyrrhizic acid, hesperidin methyl chalcone, myrecetin, natokinase, red wine poyphenols, rutin, 20-hydroxy ecdysterone Hormones—DHEA, 7-Keo DHEA, pregnenolone, melatonin Antioxidants—glutathione, alpha-lipoic acid R-lipoic acid, SOD, catalase, flavonoids, carotenoids, catechins, epicatechins.

Fat Soluble Vitamins—vitamins A, D, E, K1, K2

Water soluble Vitamins—vitamins B1, B2, B3, B5 B6 and B12, folate, pyridoaxal-5 phosphate, pantethine Vitamin Derivatives—benfotiamine Minerals—calcium, magnesium, iodine, iodide, chromium, selenium, potassium, molybdenum, manganese, iron, copper zinc, boron, vanadium, silicon, lithium, silver, strontium Fatty Acids—docosahexanoic acid, marine lipids, omega-3 and omega-6 fatty acids. blackcurrant seed oil, borage oil, evening primrose oil, hemp seed oil, cetyl myristoleate, conjugated linoleic acid, flax seed oil, phosphatidyserine, krill oil, fumaric acid, undecylenic acid, shark liver oil Carotenoids—lutein, lycopene, luteolin beta-carotene, zeaxanthin, astaxanthin Tocopherols—alpha-tocopherol, mixed tocopherols. tocotrienols Phytosterols—β-sitosterol, stigmasterol Metabolic Factors—glucosamine, chondroitin sulfate, hyaluronic acid, CoQ10, lipoic acid, beta-phenylethylamine, beta-glucan, L-carnosine, ferulic acid, gamma oryzanol, L-theanine, phenibut, forskolin, 5-hydroxy tryptophan, inositol hexaphosphate, alpha-glycerolphosphoryl choline, piracetam, L-Tyrosine, N-acetyl tyrosine, L-carnitine, adenosine triphosphate, fucoidan, TMG. DMG, vaandyl sulfate, uridine-5-monophosphate, calcium 2-AEP, collagen Type II, serapeptase, thymic protein A, uridine, L-threanine Chelators—EDTA, DMSA

Example 8 Basic Oral Nanoparticle Carrier Composition Formulation 1-60% Nutraceutical Factors (Factors in Data Array 1 such as curcumin)

20-75% Phospholipids (Lipoid Phospholipon 90 G, Lipoid Phospholipon 90 H, Lipoid S 75, Lipoid S 40, Lipoid S 80, Lipoid E 80, Lipoid Phosal 50 SA, Lipoid Phosal 53 MCT)

25-75% Lipids (safflower oil, sunflower oil, medium chain triglycerides)
20-60% Solvents and carrier Fluids (distilled water, glycerine, lipids)
0-5% Preservatives (ascorbyl palmitate, rosemary oleoresin, tocopherol, potassium sorbate)

Example 10 Examples of Nutraceutical Factors for Delivery Across the Cell Membrane Barriers Nanoparticle Delivery System Composition Data Array 6
Examples of nutraceutical factors for delivery across the cell membrane barriers nanoparticle delivery system composition include one or more the following:
Essential Fatty Acids—Omega-3 EPA and DHA, Omega-6 GLA, CLA
Phytonutrients—Curcumin, Silymarin, Andrographis, Boswell in, Green Tea Extract, Blue Corn Color, Cats Claw extract, Sambaia extract, Grape Seed Extract, Hawthorn Berry Extract
Phytochemicals—Vinpocetine, Forskolin, Ellagic Acid, Resveratrol, Quercetin
Hormones—DHEA, Pregnenolone
Antioxidants—Glutathione, R-Lipoic Acid, SOD, Catalase, Flavonoids, Carotenoids, Catechins, Epicatechins
Fat Soluble Vitamins—Vitamins A, D, E and K
Carotenoids—Lutein, Lycopene beta-Carotene, Zeaxanthin
Tocopherols—alpha-Tocopherol, Tocotrienols
Phytosterols—)3-Sitosterol, Stigmasterol
Metabolic Factors—Glucosamine, Chondroitin Sulfate, Hyaluronic Acid, CoQ10
Chelators—EDTA, DMSA Example 11

390 mg of fatty acids (high oleic acid safflower oil) was added to a vessel containing 325 mg of phospholipids (Lipoid Phospholipon 80) while stirring at low RPM. Next, 75 ml of ethanol was added to the mixture. Next, 100 mg of Reseveratrol was added to the mixture. Mixture was homogenated at 10,000 RPM for 10 minutes using a high-speed stirrer to form a pre-nanoparticle suspension emulsion. Using a probe type ultrasonic wave homogenizer in a flow through chamber the mixture was subjected to 1750 watts of ultrasonic wave treatment for 60 minutes in a flow a thorough chilled chamber under cooling. 100% of the resulting lipid structured nanoparticles passed through a filtering membrane of 0.2 µm.

Example 12

27 mg of NaOH was dissolved in 100 ml of distilled water in a vessel. Next, 100 mg of ascorbic acid and 25 mg of r-lipoic acid were added to the vesicle containing the distilled water/NAOH solution to neutralize protons in the solution giving sodium ascorbate and sodium r-lipoic acid (Sodium Lipoate). Next, 350 mg of medium chain triglycerides (Miglyol 810 N) and 325 mg of phospholipids (Lipoid Phospholipon 80) were added to the mixture followed by adding 15 mg of ethanol while stirring at low RPM. Mixture was homogenated at 10,000 RPM for 10 minutes using a high-speed stirrer to form a pre-nanoparticle suspension emulsion. Using a probe type ultrasonic wave homogenizer the mixture was subjected to 2000 watts of ultrasonic wave treatment for 60 minutes in a flow through chamber under cooling. The mean particle diameter of the resulting lipid nanostructure carrier composition was 67.80 nm when measured by a light scattering particle diameter measurement device. (Malvern Zetasizer Nano ZS)

Example 13

350 mg of medium chain triglycerides (Miglyol 810 N) was added to a vessel containing 325 mg of phospholipids (Lipoid Phospholipon 80) while stirring at low RPM. Next, 200 ml of distilled water was added to the mixture. Next, 200 mg of reduced glutathione was discharged into the mixture. Mixture was homogenated at 10,000 RPM for 10 minutes using a high-speed stirrer to form a pre-nanoparticle suspension emulsion. Using a probe type ultrasonic wave homogenizer the mixture was subjected to 2500 watts of ultrasonic wave treatment for 60 minutes under cooling. The mean particle diameter of the resulting lipid nanostructure carrier composition was 13.90 nm when measured by a light scattering particle diameter measurement device. (Malvern Zetasizer Nano ZS)

Healthy subjects were given 1000 mg of intraoral delivered reduced glutathione (GSH) lipid nanostructure carrier composition in 100 mg increments between their gums and cheeks over a period of 5 minutes through a precision dose-metering pump. Venous blood samples were drawn from the antecubital vein before administration and 44 minutes, 63 minutes and 103 minutes after intraoral GSH lipid nanostructure carrier composition administration. Total glutathione (tGSH) and GSSG were measured by the enzymatic method of Tietze. The content of GSH calculated as the difference between tGSH and GSSG are graphically displayed. Subject A and B showed a 34% and 20% increase in venous blood GSH levels after 44 minutes over their baseline GSH levels.

Example 14

3250 mg of medium chain triglycerides (Miglyol 810 N) is added to a vessel containing 3600 mg of phospholipids (Lipoid Phospholipon 80) while stirring at low RPM. Next, 2500 ml of distilled water was added to the mixture 1500 mg of DHEA was ground in a powder mill to micron size, approximately 75 micrometers. Micronized DHEA was dispersed into the mixture. Mixture was homogenated at 10,000 RPM for 15 minutes using a high-speed stirrer to form a pre-nanoparticle suspension emulsion. Pre-nanoparticle suspension emulsion is passed through 3 cycles at 1200 bars of high pressure homogenization (Avestin EmulsiFlex-D20) to produce a lipid nanostructure carrier composition of less than 75 nm average particle size.

Example 15 Lipid Structured Nanoparticle Carriers

Numerous types of nanoparticle carriers have been developed. Data Array 6 describes some of the representative different types of nanoparticle carriers.

In general, a nanoparticle carrier is expected to protect a nutraceutical factor (or drug) from degradation, enhance factor absorption by facilitating diffusion through epithelium, modify the pharmacokinetic and factor tissue distribution profile, and/or improve intracellular penetration and distribution.

Nanoparticle carriers can be designed for all possible routes of administration, generally improving both bioavailability and efficacy of the carried factor. They represent an alternative class of vehicles to liposomes to transport factors straight to the targeted diseased cells in the body.

The encapsulated or entrapped factor should be released from the nanoparticle carrier only when it will reach the biological target. Indeed, the main difficulty is to keep the factor inside such small nanoparticle carriers because of the enormous exchange surface with the surrounding external media. Thus, the release of the factor often occurs as a burst as soon as the factor-loaded nanoparticle carrier is transferred in a releasing media.

The design of nanoparticle factor carriers meets the following requirements:

a) Composition must be acceptable for use in humans (biodegradable, biocompatible, non-irritating non-toxic);

b) Size must be suitable for administration to humans by different routes and allow diffusion inside the body to reach the biological target site;

c) Blood distribution should suit the biological requirements for activity of the target; and d) The carrier must be loaded with the factor and should only release it in a controlled manner once the carrier has reached the biological target site.

Since lipids are part of living constituents, they are considered to be suitable biomaterials to form nanoparticle carriers. Many suitable lipids are available that have been used to form lipid nanoparticle carriers that are GRAS listed and entirely non-toxic to humans. Synthetic polymers offer an almost infinite array of chemical composition and structure combinations. However, only a few have the requirements that make them useful as nanoparticle factor carriers. Many polymers have toxic properties and can produce side effects in humans.

As a result, the nanoparticle carrier disclosed for use as nanoparticle carriers of nutraceutical factors in this disclosure are the lipid structured nanoparticles, solid lipid nanoparticles and lipid emulsion nanoparticles.

Example 16

Nanosphere Formulation

25%-65% active materials, flavors, sweeteners and preservatives. 35%-75% materials forming the delivery system: essential phospholipids, fatty acids, solvents. Formulation comprises: active ingredients (nutraceuticals); nanosphere (essential phospholipids—greater than 85% phosphatidylcholine; and medium chain triglycerides); sweeteners (sucralose, acesulfame K, magnasweet 110); flavors (fruit flavor, fruit juice, sweetener enhancer, bitter blocker); preservatives (potassium sorbate) and solvents (water, polysorbate 80).

Procedure:

Blend and dissolve dry powders. Blend liquids/oils/sweeteners together. Blend all mixtures; Mix completely. Grind liquid emulsion through product mill Homogenize, and then sonify emulsion with 1500 watts to 3000 watts in flow through chamber under cooling. Blend in fruit flavor and juice. The example embodies nanoparticle without surfactant, limited to phospholipids and medium chain triglycerides; and requires three dispersion techniques: milling, homogenation and ultrasonic processing. This done using cold techniques to prevent product degradation from heat.

Example 17

TABLE 1

Formulation for Men's Delivery: Table I
MENS Formula

| | weight % | ingredient |
|---|---|---|
| Actives | 2-4% | Dehydroepiandrosterone (DHEA) |
| | 2-4% | Pygeum Extract |
| | 4-7% | Saw Palmetto Berry Extract |
| | 1.5-3% | Zinc (zinc citrate) |
| | 1-2% | Boric Acid |
| | 1-2% | Icariin |
| | 4-8% | Osthole |
| NanoSpheres | 28-37% | Essential Phosholipids (greater than 85% phosphatidylcholine) Medium Chain Triglycerides |
| Sweetners | 3-7% | Sucralose, Acesulfame K Mangasweet 110 |
| Natural Flavors | 4-8% | |
| Preservatives | .1-.2% | Potassium Sorbate, Vitamin E (d-alpha tocopheryl acid succinate) |
| Solvents and Carriers | 15-35% | Water, Glycerine |

Example 18

Women's Formulation Table II
WOMENS Formula

| | | |
|---|---|---|
| Actives | 1.25-2.5% | Pregnenolone |
| | 4-7% | DIM (Diindolymethane) |
| | .5-1% | Boric Acid |
| | .1-.4% | 5 methyltetrahydrofolic acid |
| | .3-.6% | Biotin |
| | 1-2% | Icariin |
| | 3-6% | *Rhodiola rosea* extract |
| | 3-4.5% | Osthole |
| | 4-8% | *Vitex Agnus Castus* extract |
| Nanospheres | 30-40% | Essentials Phosholipids (greater than 85% phosphatidylcholine) Medium Chain Triglycerides |
| Sweetners | 2-4% | Sucralose, Acesulfame K Mangasweet 110 |
| Natural Flavors | 4-8% | |
| Preservatives | .1-.2% | Potassium Sorbate, Vitamin E (d-alpha tocopheryl acid succinate) |
| Solvents and Carriers | 15-35% | Water, Glycerine |

Example 19

Longevity Formulation: Table III
LONGEVITY formula

| | | |
|---|---|---|
| Actives | 10-15% | EDTA (calcium disodium) |
| | 4-8% | Gotu Kola extract |
| | 3-6% | Haritaki (*Terminalia chebula*) Ext |
| | 2-4% | L-Carnosine |
| | 1-3% | Na-R-Lipoic Acid |
| | 1-3% | a-Lipoic Acid |
| | 1.5-3% | Resveratrol |
| | 2-4% | Ubiquinone, CoQ10 |
| | 2-4% | Pine Bark Extract |

Longevity Formulation: Table III
LONGEVITY formula

|  |  |  |
|---|---|---|
|  | 3-6% | Green Tea Extract |
|  | 3.5-5.5% | Beta-Glucan |
|  | 3-6% | Pomegranate Extract |
|  | .3-.6% | Iodine (potassium iodide) |
| NanoSpheres | 25-35% | Essential Phospholipids (greater than 85% phosphatidylcholine) Medium Chain Triglycerides |
| Sweetners | 3-7% | Sucralose, Acesulfame K Mangasweet 110 |
| Natural Flavors | 5-12% |  |
| Preservatives | .1-.2% | Potassium Sorbate, Vitamin E (d-alpha tocopheryl acid succinate) |
| Solvents and Carriers | 10-30% | Water, Glycerine |

Example 20

Energy Formulation Table IV

|  |  |  |
|---|---|---|
|  | 1-2% | Vitamin B-6 (pyridoxine hydrochloride) |
|  | 20-40% | beta-Phenylethylamine |
|  | .015-.035% | Huperzine A |
|  | 2-4% | Bacopa Monniera extract |
|  | 1-4% | Theobromo Cacao Extract (25X) |
|  | 10-20% | Hordenine HCL |
|  | 1-3% | N-acetyltyrosine |
| Nanospheres | 25-35% | Essential Phospholipeds (greater than 85% phosphatidylcholine) Medium Chain Triglycerides |
| Sweetners | 3-7% | Sucralose, Acelsulfame K Mangasweet 110 |
| Natural Flavors | 5-12% |  |
| Preservatives | .1-.2 % | Potassium Sorbate, Vitamin E (d-alpha tocopheryl acid succinate) |
| Buffers | 1-3% | Sodium hydroxide |
| Solvents and Carriers | 7-15% | Water, Glycerine |

Example 21

Multi Formulation: Table 21
MULTI formula

|  |  |  |
|---|---|---|
| Actives | .1-.2% | Beta Carotene 1% |
|  | .1-.2% | Vitamin A Palmitate |
|  | 1.2-.5% | Vitamin B-1 thiamine HCL) |
|  | 1-3% | Vitamin B-2 (riboflavin,) |
|  | 2-4% | Vitamin B-3 (inositol hexanicotinate) |
|  | 2-4% | Vitamin B-5 (CA Panothenate ) |
|  | 1-2.5% | Vitamin B-6 (pyridoxine hydrochloride) |
|  | 1-2% | Vitamin B-5 (Pantethine) |
|  | .05-2.5% | Vitamin B-6 (pyridoxal 5 phosphate) |
|  | .02-.1% | Vitamin B-12 (Methylcobalamin) |
|  | 4-20% | Vitamin C |
|  | .3-6% | Ascrobyl Palmitate |
|  | 1-3% | Vitamin D-3 (cholicalciferol) |
|  | .02-.04% | Vitamin K1 |
|  | .0003-.0006% | Vitamin K2 |
|  | .03-.1% | 5 methyltetrahydrofolic acid |
|  | .02-.04% | Biotin |
|  | 1-2% | PABA (para-aminobenzoic acid) |
|  | .1-.3% | Boron (Boric Acid) |
|  | .01-.03% | Chromium (chromium polynicotinate) |
|  | .04-.08% | Copper Sebacate |
|  | .01-.02% | Iodine (potassium iodide) |

Multi Formulation: Table 21
MULTI formula

|  |  |  |
|---|---|---|
|  | .3-.6% | Manganese (manganese sulfate) |
|  | 01-.02% | Molybdenum (ammonium molydate ) |
|  | .01-.02% | Selenium (selenate) |
|  | .01-.02% | Vanadium (vanadyl sulphate) |
|  | 1-2.5% | Zinc (zinc citrate) |
|  | 1.75-4% | Red Plam oil super olein |
|  | 1.5-3% | Vitamin E (mixed tocopherol oil) |
|  | 2.25-5% | Vitamin E (alpha tcopherol oil) |
|  | .5-.1% | D-limone |
|  | .2-.7% | Rosemary |
| NanoSpheres | 30-40% | Essential Phospholipids (greater than 85% phosphatidylcholine) Medium Chain Triglycerides |
| Sweetners | 2.5-7.5% | Sucralose, Acesulfame K Mangasweet 110 |
| Natural Flavors | 5-10% |  |
| Preservatives | .1-.2% | Potassium Sorbate, Vitamin E (d-alpha tocopheryl acid succinate) |
| Solvents and Carriers | 15-35% | Water, |

While the apparatus and method have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

While the method and agent have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

It should also be understood that a variety of changes may be made without departing from the essence of the disclosure. Such changes are also implicitly included in the description. They still fall within the scope of this disclosure. It should be understood that this disclosure is intended to yield a patent covering numerous aspects of the disclosure both independently and as an overall system and in both method and apparatus modes.

Further, each of the various elements of the disclosure and claims may also be achieved in a variety of manners. This disclosure should be understood to encompass each such variation, be it a variation of an embodiment of any apparatus embodiment, a method or process embodiment, or even merely a variation of any element of these.

Particularly, it should be understood that as the disclosure relates to elements of the disclosure, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this disclosure is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

Finally, all referenced listed in the Information Disclosure Statement or other information statement filed with the application are hereby appended and hereby incorporated by reference; however, as to each of the above, to the extent that such information or statements incorporated by reference might be considered inconsistent with the patenting of this/these disclosure(s), such statements are expressly not to be considered as made by the applicant(s).

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, the use of the transitional phrase "comprising" is used to maintain the "open-end" claims herein, according to traditional claim interpretation. Thus, unless the context requires otherwise, it should be understood that the term "compromise" or variations such as "comprises" or "comprising", are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

The description of the present invention has been presented for purposes of illustration and description, but is not intended to be exhaustive or limiting of the invention to the form disclosed. The scope of the present invention is limited only by the scope of the following claims. Many modifications and variations will be apparent to those of ordinary skill in the art. The embodiment described was chosen and described in order to best explain the principles of the invention, the practical application, and to enable others of ordinary skill in the art to understand the invention for various embodiments with various modifications as are suited to the particular use contemplated.

What is claimed is:

1. A method for making improved lipid structural nanoparticle carrier systems comprising: combining essential phospholipids and fatty acids and solvents and using at least three production methods selected from the group consisting of high shear homogenization and ultrasonication, high pressure homogenization, microemulsions, solvent emulsification/evaporation, water-in-oil double, and milling utilizing cold techniques for formation of the lipid structural nanoparticles.

2. The method of claim 1, wherein high pressure homogenization further comprises hot homogenization and cold homogenization.

3. The method of claim 1 further comprising adding at least one nutraceutical, effective for administration to mammals.

4. The method of claim 3, further comprising adding at least an additional supplement, vitamin and related compound safe to administer to mammals.

5. The method of claim 1 wherein the nanoparticles are in the range of 20 to 60 nm.

* * * * *